US010898533B1

(12) United States Patent
Yehia et al.

(10) Patent No.: US 10,898,533 B1
(45) Date of Patent: Jan. 26, 2021

(54) MANGOSTEEN NANOPARTICLES

(71) Applicant: KING SAUD UNIVERSITY, Riyadh (SA)

(72) Inventors: Hany Mohamed Yehia, Riyadh (SA); Manal Ahmed Gasmelseed Awad, Riyadh (SA); Mohamed Fekry Serag El-Din, Shebin El-Kom (EG); Hatem Salama Mohamed Ali, Cairo (EG); Reem Atta Alajmi, Cairo (EG); Dina Mahmoud Metwally Hasanin, Zagazig (EG); Wafa Abdullah Al-Megrin, Riyadh (SA); Manal Fawzy Elkhadragy, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/752,669

(22) Filed: Jan. 26, 2020

(51) Int. Cl.
*A61K 36/38* (2006.01)
*A61K 9/51* (2006.01)
*A61P 31/04* (2006.01)

(52) U.S. Cl.
CPC ............ *A61K 36/38* (2013.01); *A61K 9/5192* (2013.01); *A61P 31/04* (2018.01); *A61K 2236/17* (2013.01)

(58) Field of Classification Search
CPC ........ A01N 37/36; A01N 25/34; A01N 65/00; A01N 59/16; A01N 65/08; A61K 9/14; A61K 2236/39; A61K 36/185; A61K 9/16; A61K 2236/51; A61K 9/5192; A61K 2236/00; A61K 31/336; A61K 33/00; A61K 9/1682; A61K 9/5115; A61K 9/5138; A61K 2236/15; A61K 2236/31; A61K 2236/33; A61K 2236/331; A61K 2236/333; A61K 2236/53; A61K 31/353; A61K 33/24; A61K 33/30; A61K 35/00; A61K 35/741; A61K 36/31; A61K 36/42; A61K 36/53; A61K 36/81; A61K 38/00; A61K 9/19; A61K 9/5026; A61K 9/5036; A61K 9/5073; A61K 9/5089; A61K 9/5146; A61K 9/5161; A61K 9/7007; A61K 36/38; A61K 2236/17; B82Y 40/00; B82Y 5/00; B82Y 30/00; C07J 63/008; C07J 53/002; A61P 31/04; A61P 35/00; A61P 1/16; A61P 31/10; A61P 39/06; A23K 10/18; A23L 33/00; A23L 33/135; B22F 1/0044; B22F 2009/245; B22F 2301/255; B22F 2998/10; B22F 9/24; B29C 67/00; C01B 2202/04; C01B 2202/06; C01B 32/152; C01B 32/16; C01B 32/174; C01G 9/02; C01P 2004/16; C01P 2004/32; C01P 2004/62; C01P 2004/64; C07C 7/005; C12P 3/00; D21H 13/50
See application file for complete search history.

(56) References Cited

U.S. PATENT DOCUMENTS

| 9,480,656 | B1 * | 11/2016 | Awad | A61K 9/5089 |
|---|---|---|---|---|
| 9,700,512 | B1 * | 7/2017 | Wagealla | A61K 31/353 |
| 9,789,146 | B1 * | 10/2017 | Awad | A61K 9/5161 |
| 10,022,412 | B2 | 7/2018 | Lee et al. | |
| 10,086,027 | B1 * | 10/2018 | Elgamal | A61K 9/7007 |
| 10,363,218 | B1 * | 7/2019 | Virk | A61K 35/741 |
| 10,442,833 | B1 * | 10/2019 | El Dib | A01N 37/36 |
| 10,588,929 | B1 * | 3/2020 | Ortashi | A61K 38/00 |
| 2003/0091417 | A1 | 5/2003 | Rojanapanthu et al. | |
| 2020/0165292 | A1 * | 5/2020 | El Dib | A01N 25/34 |
| 2020/0165293 | A1 * | 5/2020 | El Dib | A01N 25/34 |
| 2020/0165294 | A1 * | 5/2020 | El Dib | A01N 25/34 |

FOREIGN PATENT DOCUMENTS

| CN | 1436786 A | 8/2003 |
|---|---|---|
| CN | 105815497 A | 8/2016 |
| JP | 09110688 A | 4/1997 |
| KR | 101989971 b1 | 6/2019 |

OTHER PUBLICATIONS

Lim, Y. S. et al., "Antioxidant capacity and antibacterial activity of different parts of mangosteen (*Garcinia mangostana* Linn.) extracts," Fruits, 2013, vol. 68(6), pp. 483-489.

"Natural Home Cures Freeze Dried Rich Pericarp Mangosteen," Copyright © 2019 Welcome to Natural Home Cures Freeze Dried Rich Pericarp Mangosteen, website: http://www.mymangosteencures.net last accessed: Jan. 8, 2020.

Pothitirat, W., et al., "Comparison of bioactive compounds content, free radical scavenging and anti-acne inducing bacteria activities of extracts from the mangosteen fruit rind at two stages of maturity," Fioterapia, vol. 80, pp. 442-447, 2009.

Suksamrarn, S. et al., "Xanthones from the green fruit hulls of Garcinia mangostana," J Nat Prod., vol. 65, 99. 761-763, 2002.

Jung, H. A. et al., "Antioxidant xanthones from the pericarp of Garcinia mangostant (Mangosteen)," J. Agri. Food Chem., vol. 54, pp. 2077-2082, 2006.

(Continued)

*Primary Examiner* — Aaron J Kosar
(74) *Attorney, Agent, or Firm* — Nath, Goldberg & Meyer; Richard C. Litman (57) ABSTRACT

Mangosteen nanoparticles and methods of synthesizing Mangosteen nanoparticles are provided. The Mangosteen nanoparticles may be synthesized by drying Mangosteen, *Garcinia mangostana* fruit, grinding the dried Mangosteen to form powdered Mangosteen, suspending the powdered Mangosteen in a solvent to form a first Mangosteen solution, spraying the Mangosteen solution into boiling water under ultrasonic conditions to form a second Mangosteen solution, resting the second Mangosteen solution at room temperature (about 20° C.), and freeze-drying the second Mangosteen solution to obtain Mangosteen nanoparticles. The drying step may include either air-drying or freeze-drying the Mangosteen. The Mangosteen fruit peel may be used in the drying step instead of the inner Mangosteen fruit. The resulting nanoparticles may be used in pharmaceutical compositions, and may be useful for their antioxidant and antibacterial activities.

19 Claims, 4 Drawing Sheets

(56) References Cited

OTHER PUBLICATIONS

Chen, L. et al., "Anti-inflammatory activity of mangostins from *Garcinia mangostana*," Food Chem Toxicol. vol. 46, pp. 688-693, 2008.

Zarena, A. S. and Sankar, K. U., "A study of antioxidant properties from *Garcinia mangostana* L. pericarp extract," Acta Sci. Pol., Technol. Aliment., vol. 8(1), pp. 23-34, 2009.

* cited by examiner

*Staphylococcus aureus*

FIG. 5A

*Micrococcus luteus*

FIG. 5B

*Listeria monocytogenes*

FIG. 5C

*Enterecoccus faecium*

FIG. 5D

*Bacillus cereus*

MANGOSTEEN NANOPARTICLES

BACKGROUND

1. Field

The disclosure of the present patent application relates to nanotechnology, and particularly to Mangosteen nanoparticles, methods of synthesizing Mangosteen nanoparticles, and the use of Mangosteen nanoparticles as antibacterial agents.

2. Description of the Related Art

Recently, nanoparticles have demonstrated important uses in a variety of fields. Nanoparticles have been used in a vast array of applications, including electronics, sensing, optics, and medicine.

Synthesis of nanoparticles has been achieved by a variety of methods, including physicochemical, thermal decomposition, electrochemical, microwave assisted, sonochemical, solvothermal, photosynthesis, photochemical reduction, chemical reduction and continuous-flow methods. These methods are often costly or produce by-products that pose increased risks to human health and the environment.

In recent years, green or environmentally friendly chemical methods have been developed to prepare nanoparticles using plant extracts. Green chemistry has the advantage of being fast, environmentally friendly, and economical. However, the rise of green methods of preparing nanoparticles has also demonstrated that the activities and characteristics of the nanoparticles vary significantly, depending upon the detailed method of synthesis and specific plant extract used.

The Mangosteen (*Garcinia mangostana* L.), is alternatively known as the "queen fruit" for its unique flavor. The milky white portion of the Mangosteen is the edible portion, while the dark red peel is inedible, and can have approximately twice the mass of the edible portion. Bioactive compounds have been found within the Mangosteen peel that demonstrate potential uses as functional food additives or as therapeutic agents, including phenolic acids, tannins, xanthones, anthocyanins, and others. Compounds isolated from Mangosteen peel have been shown to have antimicrobial, antioxidant, and anti-inflammatory effects.

Thus, Mangosteen nanoparticles, methods of synthesizing Mangosteen nanoparticles, and methods of using Mangosteen nanoparticles as antibacterial agents solving the aforementioned problems are desired.

SUMMARY

The Mangosteen nanoparticles may be synthesized by drying Mangosteen (*Garcinia mangostana*) fruit, grinding the dried Mangosteen fruit to form powdered Mangosteen, suspending the powdered Mangosteen in a solvent to form a first Mangosteen solution, spraying the Mangosteen solution into boiling water under ultrasonic conditions to form a second Mangosteen solution, resting the second Mangosteen solution at room temperature (about 20° C.), and freeze-drying the second Mangosteen solution to obtain Mangosteen nanoparticles. The drying step may include either air-drying or freeze-drying the Mangosteen. The solvent may be any suitable solvent, including but not limited to methanol. In an embodiment, 400 mg of powdered Mangosteen may be suspended in 20 ml solvent. The spraying step may include spraying the Mangosteen solution dropwise into 50 ml boiling water at a flow rate of 0.2 ml/min for 5 minutes. The ultrasonic conditions may include an ultrasonic power of 750 W and a frequency of 20 kHz. After the spraying step, the second Mangosteen solution may be sonicated for 20 minutes. The resting step may include stirring the second Mangosteen solution at 200-800 rpm for approximately 15 minutes. In an embodiment, the peel of the Mangosteen fruit may be used in the drying step, instead of the Mangosteen fruit.

An embodiment of the present subject matter is directed to a pharmaceutical composition including the Mangosteen nanoparticles and a pharmaceutically acceptable carrier.

An embodiment of the present subject matter is directed to a method of making a pharmaceutical composition including mixing the Mangosteen nanoparticles under sterile conditions with a pharmaceutically acceptable carrier and preservatives, buffers, or propellants to create the pharmaceutical composition; and providing the pharmaceutical composition in a form suitable for daily, weekly, or monthly administration.

An embodiment of the present subject matter is directed to a method of inhibiting bacterial growth, including administering to a subject in need thereof a therapeutically effective amount of a pharmaceutical composition according to the present subject matter.

These and other features of the present subject matter will become readily apparent upon further review of the following specification.

DETAILED DESCRIPTION OF THE PREFERRED EMBODIMENTS

The Mangosteen nanoparticles may be synthesized by drying Mangosteen (*Garcinia mangostana*) fruit, grinding the dried Mangosteen to form powdered Mangosteen, suspending the powdered Mangosteen in a solvent to form a first Mangosteen solution, spraying the Mangosteen solution into boiling water under ultrasonic conditions to form a second Mangosteen solution, resting the second Mangosteen solution at room temperature (about 20° C.), and freeze-drying the second Mangosteen solution to obtain Mangosteen nanoparticles. The drying step may include either air-drying or freeze-drying the Mangosteen. The solvent may be any suitable solvent, including but not limited to methanol. In an embodiment, about 400 mg of powdered Mangosteen may be suspended in about 20 ml solvent. The spraying step may include spraying the Mangosteen solution dropwise into about 50 ml boiling water at a flow rate of about 0.2 ml/min for about 5 minutes. The ultrasonic conditions may include an ultrasonic power of about 750 W and a frequency of about 20 kHz. After the spraying step, the second Mangosteen solution may be sonicated for about 20 minutes. The resting step may include stirring the second Mangosteen solution at about 200 rpm to about 800 rpm for approximately 15 minutes. In an embodiment, the peel of the Mangosteen fruit may be used in the drying step, instead of the Mangosteen fruit.

In an embodiment, the freeze-dried Mangosteen nanoparticles may have an average particle diameter of about 123.1 nm with a polydispersity of about 0.382.

In an embodiment, the air-dried Mangosteen nanoparticles may have an average particle diameter of about 153.1 nm with a polydispersity of about 0.241.

As used herein, the term "about," when used to modify a numerical value, means within ten percent of that numerical value.

An embodiment of the present subject matter is directed to a pharmaceutical composition comprising the Mangosteen nanoparticles and a pharmaceutically acceptable carrier.

An embodiment of the present subject matter is directed to a method of making a pharmaceutical composition including mixing the Mangosteen nanoparticles with a pharmaceutically acceptable carrier. For example, the method of making a pharmaceutical composition can include mixing the Mangosteen nanoparticles under sterile conditions with a pharmaceutically acceptable carrier with preservatives, buffers, and/or propellants to create the pharmaceutical composition.

An embodiment of the present subject matter is directed to a pharmaceutical composition including the Mangosteen nanoparticles. To prepare the pharmaceutical composition, the Mangosteen nanoparticles, as the active ingredient, are intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The Mangosteen nanoparticles can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the Mangosteen nanoparticles or an amount effective to treat a disease, such as a bacterial infection, may be determined initially from the Examples described herein and adjusted for specific targeted diseases using routine methods.

The Mangosteen nanoparticles can be administered to a subject in need thereof. In an embodiment, the Mangosteen nanoparticles can be administered to a subject in need thereof to inhibit bacterial growth and/or prevent or treat a bacterial infection. In a further non-limiting embodiment, the bacterium can be a gram-positive bacterium. The gram positive bacterium may be a bacterium selected from the group consisting of *Staphylococcus aureus, Listeria monocytogenes, Bacillus cereus, Micrococcus luteus,* and *Enterococcus faecium*.

An embodiment of the present subject matter is directed to a method of preventing bacterial growth, comprising administering to a subject in need thereof a therapeutically effective amount of the pharmaceutical composition according to the present subject matter.

The Mangosteen nanoparticles or pharmaceutical compositions thereof can be administered to a subject by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

The following examples illustrate the present subject matter.

Example 1

Synthesis of Mangosteen Nanoparticles

Fresh Mangosteen (*Garcinia mangostana*) fruit was washed with deionized water several times to remove dust particles. The peel of the fruit was then separated into two samples. The first sample was air-dried to remove residual moisture, cut into small pieces, and stored in an air-tight container. The second sample was cut into small pieces, loaded onto a tray, and freeze-dried on a shelf in a freeze dryer (Labconco, USA). Both samples were then ground to form a first and a second Mangosteen powder.

The first and second Mangosteen powders (400 mg) were then separately dissolved in methanol (20 ml) and the resulting first solutions, respectively, were sprayed dropwise into boiling water (50 ml) at a flow rate of 0.2 ml/min for 5 min under ultrasonic conditions (ultrasonic power of 750 W and frequency of 20 kHz) to produce second solutions. The second solutions were then sonicated for 20 minutes, stirred at 200-800 rpm at room temperature (20° C.) for approximately 15 minutes, and freeze dried to obtain air-dried and freeze-dried Mangosteen nanoparticles, respectively.

Example 2

Characterization of Mangosteen Nanoparticles

Figure 1:
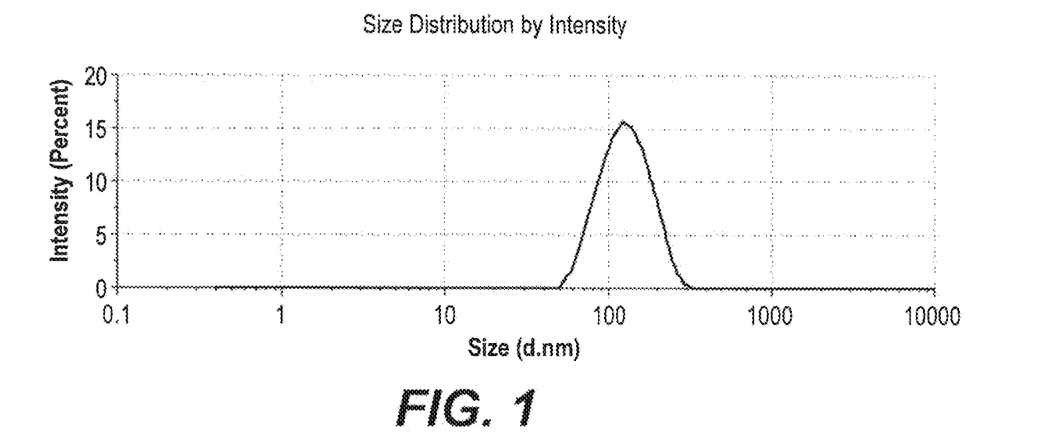
FIG. 1 depicts a zetasizer spectrum of freeze-dried Mangosteen peel nanoparticles.
Figure 2:
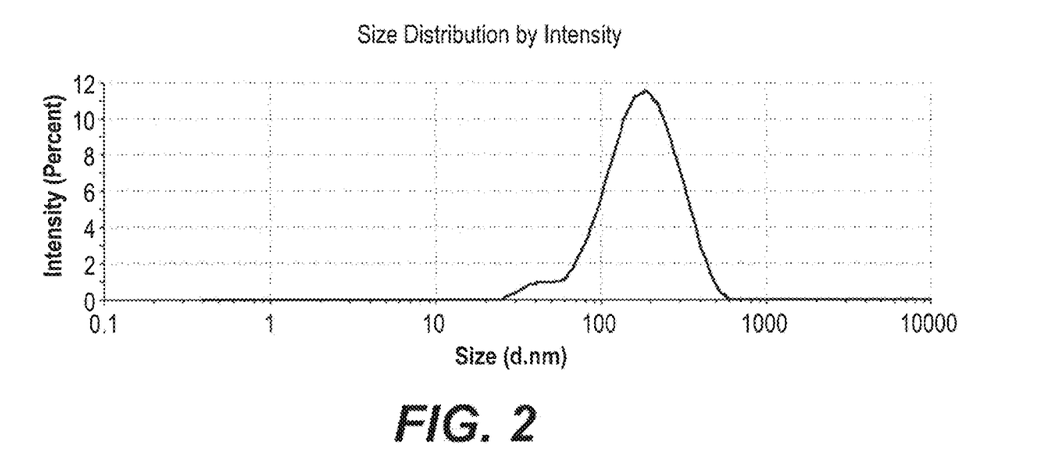
FIG. 2 depicts a zetasizer spectrum of air-dried Mangosteen peel nanoparticles.

Dynamic Light Scattering (DLS) analysis was performed using a Zetasizer to obtain the average diameter of the Mangosteen nanoparticles synthesized according to the method of Example 1. The results for the freeze-dried Mangosteen peel nanoparticles and for the air-dried Mangosteen peel nanoparticles are depicted in FIGS. 1-2 and Tables 1-2, respectively. In summary, the average particle diameter of the freeze-dried Mangosteen peel nanoparticles was 123.1 nm with a polydispersity (PDI) of 0.382; while the average particle diameter of the air-dried Mangosteen peel nanoparticles was 153.1 nm with a PDI of 0.241.

TABLE 1

Zetasizer Measurement of Freeze-Dried Mangosteen Peel Nanoparticles

|  |  |  | Size (d.nm) | % Intensity | St Dev (d.nm) |
|---|---|---|---|---|---|
| Z-Average (d. nm) | 123.1 | Peak 1 | 132.5 | 100 | 45.8 |
| PDI | 0.382 | Peak 2 |  |  |  |
| Intercept | 0.939 | Peak 3 |  |  |  |
| Quality | Good |  |  |  |  |

TABLE 1

Zetasizer Measurement of Air-Dried Mangosteen Peel Nanoparticles

|  |  |  | Size (d.nm) | % Intensity | St Dev (d.nm) |
|---|---|---|---|---|---|
| Z-Average (d. nm) | 153.1 | Peak 1 | 191.3 | 100 | 957 |
| PDI | 0.241 | Peak 2 |  |  |  |
| Intercept | 0.942 | Peak 3 |  |  |  |
| Quality | Good |  |  |  |  |

Figure 3A:
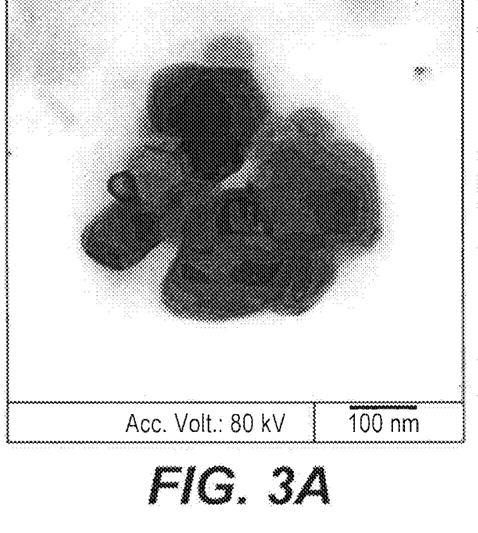
FIG. 3A depicts a transmission electron micrograph of freeze-dried Mangosteen peel nanoparticles.
Figure 3B:
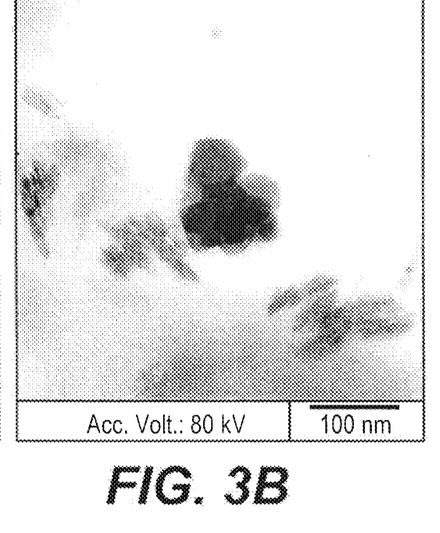
FIG. 3B depicts a transmission electron micrograph of freeze-dried Mangosteen peel nanoparticles.
Figure 4A:
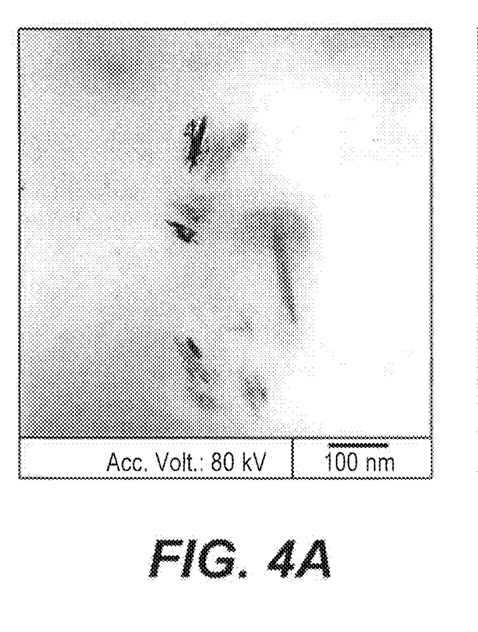
FIG. 4A depicts a transmission electron micrograph of air-dried Mangosteen peel nanoparticles.
Figure 4B:
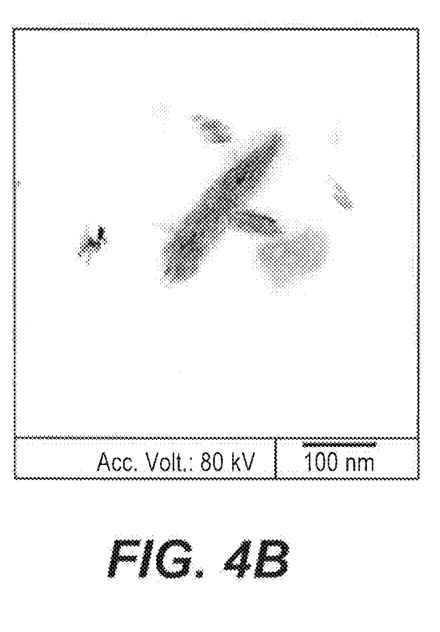
FIG. 4B depicts a transmission electron micrograph of air-dried Mangosteen peel nanoparticles.
Figure 5A:
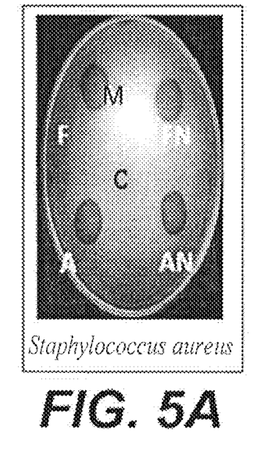
FIG. 5A depicts a petri dish demonstrating the zone of inhibition of freeze-dried Mangosteen peel nanoparticles and air-dried Mangosteen peel nanoparticles against *Staphylococcus aureus*.
Figure 5B:
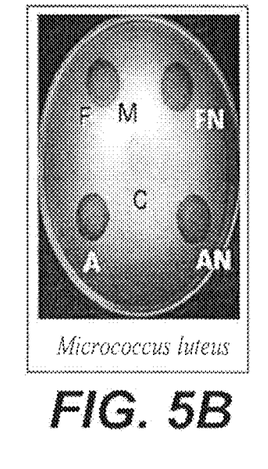
FIG. 5B depicts a petri dish demonstrating the zone of inhibition of freeze-dried Mangosteen peel nanoparticles and air-dried Mangosteen peel nanoparticles against *Micrococcus luteus*.
Figure 5C:
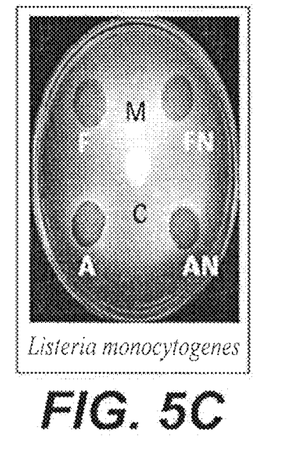
FIG. 5C depicts a petri dish demonstrating the zone of inhibition of freeze-dried Mangosteen peel nanoparticles, air-dried Mangosteen peel nanoparticles against *Listeria monocytogenes*.
Figure 5D:
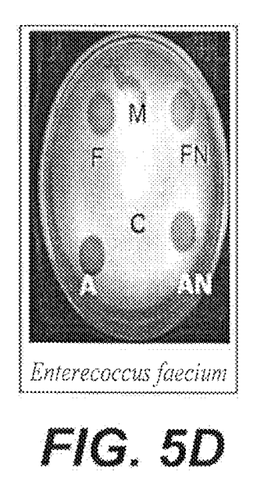
FIG. 5D depicts a petri dish demonstrating the zone of inhibition of freeze-dried Mangosteen peel nanoparticles and air-dried Mangosteen peel nanoparticles against *Enterococcus faecium*.
Figure 5E:
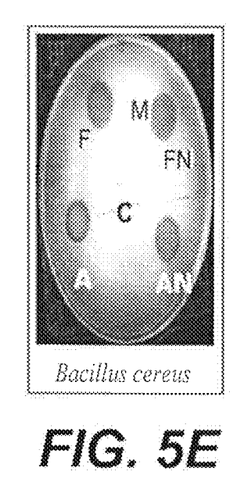
FIG. 5E depicts a petri dish demonstrating the zone of inhibition of freeze-dried Mangosteen peel nanoparticles and air-dried Mangosteen peel nanoparticles against *Bacillus cereus*.

Transmission electron microscopy (TEM) was used to obtain essential information regarding the Mangosteen peel nanoparticle sizes and morphologies (See FIGS. 3A-4B). The freeze-dried Mangosteen peel nanoparticles examined by TEM exhibited spherical and rod-shaped morphology (FIGS. 3A-3B). Additionally, all the Mangosteen peel nanoparticles were similar in size. The air-dried Mangosteen peel nanoparticles investigated by TEM exhibited only rod-shaped morphology and the particles were of various sizes (FIGS. 4A-4B).

Example 3

Synthesis of Mangosteen Extracts and Mangosteen Nanoparticle Extracts

To better understand the differences between the air-dried and freeze-dried Mangosteen nanoparticles, Mangosteen extracts were prepared using the first and second Mangosteen powders synthesized according to Example 1 and the freeze-dried and air-dried Mangosteen nanoparticles synthesized according to Example 1. Briefly, 100 mg/ml of the first and second powder and the freeze-dried and air-dried Mangosteen nanoparticles were added to respective containers with 50 ml methanol. These mixtures were then incubated at room temperature for 24 hours on a shaker, followed by centrifugations (10,000 rpm for 15 min) to obtain supernatants. The supernatants were filtered using Whatman No. 41 filter paper, adjusted to 50 ml volume, and the resulting Mangosteen Extracts were stored at −20° C.

Example 4

Antioxidant Activity of Mangosteen Extracts

The content of total phenolic compounds in the Mangosteen Extracts prepared according to Example 3 was determined using the Folin-Ciocalteu method (W. C H et al., "Improved production of caffeine acid derivatives in suspension cultures of *Echinacea purpurea* by medium replenishment strategy," Arch. Pharm. Res., vol. 30, pp. 945-949, 2007). Briefly, a volume of 2.5 ml of distilled water and 0.1 ml of a sample extract (either air-dried or freeze-dried extract) were both added to a test tube, followed by the addition of 0.1 ml of undiluted Folin-Ciocalteu reagent (Sigma-Aldritch). The resulting solution was mixed thoroughly and allowed to stand for 6 minutes before 0.5 ml of a 20% sodium carbonate solution was added. Color developed after 30 minutes at room temperature, and absorbance was measured at 760 nm using a spectrophotometer (Milton Roy Spectronic 1201, USA). A blank sample was prepared using 0.1 ml of methanol in the place of the extract. Measurements were compared to a calibration curve generated by gallic acid solutions, and values were expressed as gallic acid equivalents per gram of dry weight sample.

The total flavonoid content of the Mangosteen Extracts prepared according to Example 3 was determined by the aluminum chloride colorimetric method (S. A. Baba and S. A. Malik, "Determination of total phenolic and flavonoid content, antimicrobial and antioxidant activity of a root extract of *Arisaema jacquemontii* Blume," J Taibah Univ Sci., vol. 9, pp. 449-454, 2015). Briefly, 50 µl of a sample extract (either air-dried or freeze-dried extract) was mixed with 4 ml of distilled water, and then further mixed with 0.3 ml of 5% $NaNO_2$ solution. A 0.3 ml volume of 10% $AlCl_3$ solution was added after 5 minutes of incubation, and the mixture was allowed to stand for 6 minutes. Then, 2 ml of a 1 mol/L NaOH solution was added to the mixture, and the final volume of the mixture was brought up to 10 ml using distilled water. The mixture was allowed to stand for 15 minutes and absorbance was measured at 510 nm. The total flavonoid content was calculated from a calibration curve and the result was expressed as mg rutin equivalent per g dry weight or mg catechin equivalent per g dry weight.

The ability of the Mangosteen Extracts prepared according to Example 3 to scavenge DPPH (2,2-diphenyl-1-picryl-hydrazyl) radicals was determined according to the method of Akillioglu and Karakaya (H. G. Akillioglu and S. Karakaya, "Changes in Total Phenols, Total Flavonoids, and Antioxidant Activities of common Beans and Pinto beans after Soaking, cooking, and in vitro Digestion Process," Food Sci Biotechnol., vol. 19(3): pp. 633-639, 2010). A 0.08 mM DPPH radical solution was prepared in methanol and 950 µL of this DPPH stock solution was added to 50 µl of each extract, followed by incubation for 5 minutes. Exactly 5 minutes later, absorbance readings were performed at 515 nm (Cary 50 Scan; Varian). The antioxidant activity (AA) was expressed as percent inhibition of DPPH radical activity using Equation 1, where $A_{sample}$ is the absorbance of the sample at t=5 minutes and $A_{control}$ is the absorbance of the control.

$$AA = 100 - \left[100X \frac{A_{sample}}{A_{control}}\right] \quad \text{Equation 1}$$

An ABTS+ assay (2,4,6-Tri(2-Pyridyl)-s-triazine radical scavenging assay) was performed according to the method described by Gouveia and Castilho (S. Gouveia and P. C. Castilho, "Antioxidant potential of *Artemisia argentea* L'Hér alcoholic extract and its relation with the phenolic composition," Food Res Int., vol. 14, 44, pp. 1620-1631, 2011). ABTS+ radical solution was prepared by mixing 50 mL of 2 mM ABTS solution with 200 µL of 70 mM potassium persulfate solution. This mixture was stored in the dark for 16 h at room temperature and was then maintained in this form for two days. For each analysis, the ABTS+ solution was diluted with pH 7.4 phosphate buffered saline (PBS) solution to an initial absorbance of 0.700±0.021 at 734 nm. This solution was prepared fresh for each set of analyses. To determine antiradical scavenging activity, an aliquot of 100 µL of each of the Mangosteen Extracts prepared according to Example 3 was added to 1.8 mL of ABTS+ solution and the absorbance decrease at 734 nm was recorded over a period of 6 min. The results were expressed as µmol trolox equivalent per g of dried sample (mmol eq. trolox/g) based on the trolox calibration curve.

The ferric reducing antioxidant power (FRAP) assay was performed according to the procedure described by Benzie and Strain (I. F. F. Benzie and J. J. Strain, "The ferric reducing ability of plasma (FRAP) as a measure of "antioxidant power": the FRAP assay," *Anal Biochem.*, vol. 239, pp. 70-76, 1996). The FRAP reagent included 300 mM acetate buffer at pH 3.6 and 10 mM tripyridyl triazine (TPTZ) in 40 mM HCl/20 mM FeCl3 at a ratio of 10:1:1 (v/v/v). FRAP reagent (3 mL) was mixed with 100 µL of each of the Mangosteen Extracts prepared according to Example 3 in a test tube, vortexed, and incubated at 37° C. for 30 min in a water bath. Reduction of ferric-tripyridyl-triazine to the ferrous complex resulted in the formation of an intense blue color, which was measured using a UV-vis spectrophotometer (Varian Cary 50) at 593 nm after 4 min. The results were expressed as mmol trolox equivalent per g of dried sample (mmol eq. trolox/g).

The results of these experiments are summarized in Table 3 (all data shown are means of three replicates, and are reported as mean standard deviation). In summary, the total phenols that were detected in the freeze-dried Mangosteen peel nanoparticle methanol-based extract was 1112.646±1.842 mg gallic acid/g sample. This quantity was larger than that found in the normal freeze-dried Mangosteen peel extract, which was 815.311±3.935 mg gallic acid/g sample. The total phenols in the air-dried Mangosteen peel nanoparticle extract did not exceed 479.744±2.564 mg gallic acid/g sample. The total flavonoid content in the freeze-dried Mangosteen peel nanoparticle extract and the freeze-dried Mangosteen peel extract was almost equal, and both values were greater than that found in the air-dried Mangosteen peel nanoparticle extract. The antioxidant activity (i.e., free-radical scavenging (DPPH)) of the freeze-dried Mangosteen peel nanoparticle extract was 95.707±0.070%, whereas this value in the air-dried Mangosteen nanoparticle extract was 94.303±0.074%. The ABTS value in the freeze-dried Mangosteen nanoparticle extract was 42.753±0.200 (g trolox/g sample), whereas this value in the air-dried Mangosteen peel nanoparticle extract was 16.069±0.424 (g trolox/g sample). Ferric reducing antioxidant power (FRAP) of freeze-dried Mangosteen nanoparticle extract was 17.806±0.056 (g trolox/g sample), whereas this value in air-dried Mangosteen nanoparticle extracts was 6.696±0.085 (g trolox/g sample). Generally, the measured antioxidant activity of the freeze-dried Mangosteen nanoparticle extracts was higher than that of the air-dried Mangosteen nanoparticle extracts. This result supports the improved antimicrobial activity of the freeze-dried Mangosteen nanoparticles discussed in Example 5.

TABLE 2

Total Phenols, Flavonoids, and Antioxidant Activity of Mangosteen Extracts and Mangosteen Nanoparticle Extracts

| Sample | T. Phenols (mg gallic acid/g sample) | T. Flavonoids (mg cateehin/g sample) | DPPH (%) |
|---|---|---|---|
| Air-Dried Mangosteen | 401.303 ± 14.498 | 1.057 ± 0.119 | 94.775 ± 0.122 |
| Air-Dried Mangosteen Nanoparticles | 479.744 ± 2.564 | 4.711 ± 0.207 | 94.303 ± 0.074 |
| Freeze-Dried Mangosteen | 815.311 ± 3.935 | 15.394 ± 1.496 | 94.643 ± 0.128 |
| Freeze-Dried Mangosteen Nanoparticles | 1112.646 ± 1.842 | 14.154 ± 0.119 | 95.707 ± 0.070 |

| Sample | ABTS (g trolox/g sample) | FRAP (g trolox/g sample) |
|---|---|---|
| Air-Dried Mangosteen | 13.075 ± 0.534 | 5.728 ± 0.152 |
| Air-Dried Mangosteen Nanoparticles | 16.069 ± 0.424 | 6.696 ± 0.085 |
| Freeze-Dried Mangosteen | 29.943 ± 0.058 | 12.982 ± 0.368 |
| Freeze-Dried Mangosteen Nanoparticles | 42.753 ± 0.200 | 17.806 ± 0.056 |

Example 5

Antimicrobial Activity of Mangosteen Nanoparticles

The disk diffusion method was used to test the antibacterial activity of the Mangosteen nanoparticles. *Staphylo-* coccus aureus ATCC 29737, *Listeria monocytogenes* ATCC 19114, *Bacillus cereus* ATCC 11778, *Micrococcus luteus* (local isolate), and *Enterococcus faecium* (local isolate) were obtained from the laboratory of Food Microbiology, College of Food and Agricultural Sciences, King Saud University, in Riyadh, Saudi Arabia. Briefly, a standardized inoculum (100 μl of overnight culture of any bacteria to be tested containing approximately $10^6$ colony forming units (CFUs) per ml) was swabbed onto the surface of Muller Hinton agar plates (Oxoid, CM0337, 150-mm plate diameter). Filter paper disks impregnated with a standardized concentration in 100 μl (100 mg/ml) of either freeze-dried (FN) or air-dried (AN) Mangosteen nanoparticles were placed onto the surface and compared to freeze-dried (F) and air-dried (A) Mangosteen extracts. Disks saturated with methanol were used as a control (C). The size of the zone of inhibition surrounding the disk was measured after overnight incubation at 37° C. for 24 hours.

The results of this experiment are depicted in FIGS. 5A-5E and clearly demonstrate the inhibitory effect of Mangosteen nanoparticles on the growth of the tested bacteria. Both freeze-dried and air-dried Mangosteen nanoparticles induced a large inhibition zone against all of the gram-positive bacteria tested.

A further experiment was conducted to measure the effect of Mangosteen nanoparticles on protein formation in various gram-positive bacteria. According to a modification of the method described by Yehia and Al-Dagal (H. M. Yehia and M. M. Al-Dagal, "Prevalence of *Campylobacter jejuni* in chicken produced by major poultry companies in Saudi Arabia," Int J Food Contam., vol. 1, pp. 2, 2014.), an overnight culture of each bacterium (100 μl) was inoculated into a 10-ml volume of fresh medium (brain heart infusion, Oxoid, CM1135) supplemented with methanol (1 ml) as a control, or brain heart infusion medium, containing either air-dried or freeze-dried Mangosteen Extracts. This mixture was then sterilized by filtration through a 0.45 μm Millipore filter. All strains of bacteria were grown at 37° C. for 24 h. Cells were then collected and weighed, and 250 mg of cells were then suspended in 100 μL of TES buffer (50 mM tris HCl, pH 8, 1 mM EDTA, 25% sucrose). Twenty microliters of lysozyme (50 mg/ml) was added to the suspended cells in the TES buffer and incubated at 37° C. for 30 min. Five to ten microliters of 20% SDS was then added, and the contents were mixed until the cells were clearly visible. The contents were stored at −20° C. until use. Twenty-five microliters of the extracts (bacteria in normal medium with ethanol, bacteria with air-dried Mangosteen nanoparticles, or bacteria with freeze-dried Mangosteen nanoparticles) specific to each of the five strains of bacteria tested was loaded onto SDS-PAGE. Electrophoresis was performed at 25° C. in a vertical tank apparatus using a constant voltage power supply until a bromophenol blue tracking dye reached the bottom of the gel. Gels were stained with 0.25% Coomassie brilliant blue R-250 (Bio-Rad, Marnesla-Coquette, France) in water:methanol:acetic acid (6.5:2.5:1) for 18 h at room temperature. Gel destaining was performed by continuous agitation in a methanol:acetic acid:water (20:10:70 v/v/v) solvent until obvious bands of proteins were obtained. Whole-cell protein profiles of tested bacteria were compared to air-dried and freeze-dried Mangosteen nanoparticles, and the formation of protein bands was observed following SDS-PAGE.

Figure 6:
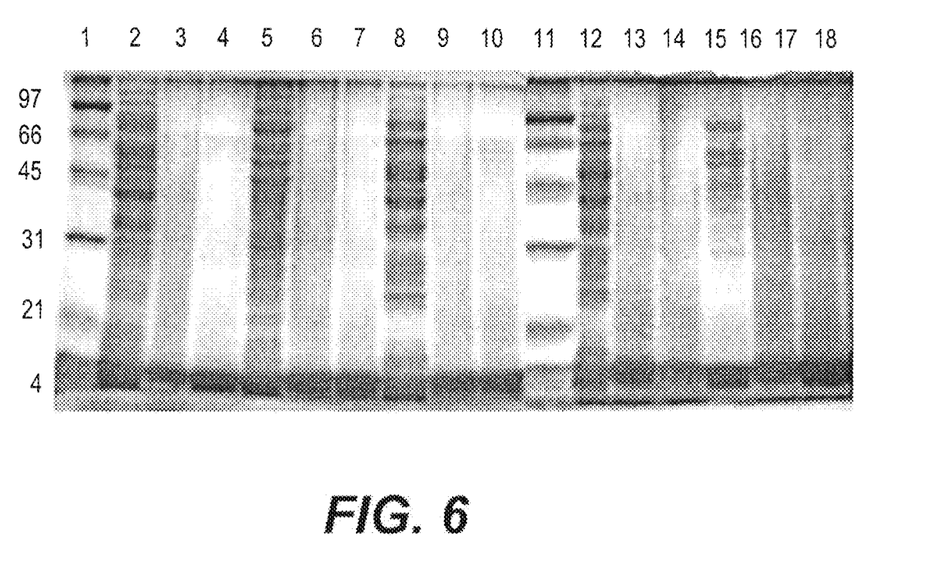
FIG. 6 depicts a total protein profile of gram-positive pathogenic bacteria treated with freeze-dried Mangosteen peel nanoparticles and air-dried Mangosteen peel nanoparticles.

The results of this experiment are depicted in FIG. 6, illustrating on an SDS-polyacrylamide gel the effect of Mangosteen nanoparticles on the growth and protein formation of various gram-positive bacteria. The whole proteins of all bacterial strains tested almost completely vanished in all lanes where the bacteria were exposed to either the air-dried or the freeze-dried Mangosteen nanoparticles (See lanes 3, 4, 6, 7, 9, 10, 13, 14, 16 and 17). In comparison, the lanes containing controls strains exhibited normal protein bands (See lanes 2, 5, 8, 12, and 15).

It is to be understood that the Mangosteen nanoparticles are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing Mangosteen nanoparticles, comprising:
   (a) drying Mangosteen fruit;
   (b) grinding the dried Mangosteen fruit to produce powdered Mangosteen;
   (c) suspending the powdered Mangosteen in a solvent to form a first Mangosteen solution;
   (d) spraying the first Mangosteen solution into boiling water under ultrasonic conditions to form a second Mangosteen solution;
   (e) resting the second Mangosteen solution at room temperature; and
   (f) freeze-drying the second Mangosteen solution to obtain Mangosteen nanoparticles.

2. The method of synthesizing Mangosteen nanoparticles as recited in claim 1, wherein the drying step comprises air-drying the Mangosteen fruit.

3. The method of synthesizing Mangosteen nanoparticles as recited in claim 2, wherein the Mangosteen nanoparticles have an average particle diameter of 153.1 nm and a polydispersity of 0.241.

4. The method of synthesizing Mangosteen nanoparticles as recited in claim 1, wherein the drying step comprises freeze-drying the Mangosteen fruit.

5. The method of synthesizing Mangosteen nanoparticles as recited in claim 4, wherein the Mangosteen nanoparticles have an average particle diameter of 123.1 nm and a polydispersity of 0.382.

6. The method of synthesizing Mangosteen nanoparticles as recited in claim 1, wherein the solvent comprises methanol.

7. The method of synthesizing Mangosteen nanoparticles as recited in claim 1, wherein the Mangosteen fruit comprises a white, inner portion of the Mangosteen fruit.

8. The method of synthesizing Mangosteen nanoparticles as recited in claim 1, wherein the Mangosteen fruit comprises Mangosteen fruit peel.

9. The method of synthesizing Mangosteen nanoparticles as recited in claim 1, wherein 400 mg of powdered Mangosteen is suspended in 20 ml solvent.

10. The method of synthesizing Mangosteen nanoparticles as recited in claim 1, wherein the spraying step further comprises spraying the first Mangosteen solution dropwise into 50 ml boiling water at a flow rate of 0.2 ml/min for 5 minutes.

11. The method of synthesizing Mangosteen nanoparticles as recited in claim 1, wherein the ultrasonic conditions include an ultrasonic power of 750 W and a frequency of 20 kHz.

12. The method of synthesizing Mangosteen nanoparticles as recited in claim 1, wherein the second Mangosteen solution is sonicated for 20 minutes before the resting step.

13. The method of synthesizing Mangosteen nanoparticles as recited in claim 1, wherein the resting step further comprises stirring the second Mangosteen solution at 200-800 rpm for about 15 minutes.

14. A method of inhibiting bacterial growth in a subject in need thereof comprising: administering an effective amount of the Mangosteen nanoparticles of claim 1.

15. The method of claim 14, wherein the bacterium is selected from the group consisting of *Staphylococcus aureus, Listeria monocytogenes, Bacillus cereus, Micrococcus luteus,* and *Enterococcus faecium.*

16. Mangosteen nanoparticles synthesized according to the method of claim 1.

17. The Mangosteen nanoparticles of claim 16, wherein the Mangosteen fruit was air-dried.

18. The Mangosteen nanoparticles of claim 16, wherein the Mangosteen fruit was freeze-dried.

19. The Mangosteen nanoparticles of claim 16, wherein the Mangosteen fruit used to synthesize the Mangosteen nanoparticles was Mangosteen fruit peel.

\* \* \* \* \*

UNITED STATES PATENT AND TRADEMARK OFFICE
CERTIFICATE OF CORRECTION

PATENT NO. : 10,898,533 B1  
APPLICATION NO. : 16/752669  
DATED : January 26, 2021  
INVENTOR(S) : Hany Mohamed Yehia et al.

Page 1 of 1

It is certified that error appears in the above-identified patent and that said Letters Patent is hereby corrected as shown below:

(72) Inventors: Reem Atta Alajmi, Cairo, (EG) should be: Reem Atta Alajmi, Riyadh (SA)

Signed and Sealed this  
Twenty-third Day of March, 2021

Drew Hirshfeld  
*Performing the Functions and Duties of the*  
*Under Secretary of Commerce for Intellectual Property and*  
*Director of the United States Patent and Trademark Office*